United States Patent [19]

Tezuka et al.

[11] 4,251,497
[45] Feb. 17, 1981

[54] METHOD FOR MEASURING THE BASIC AMOUNT IN BASIC ALUMINUM SULFATE SOLUTION FOR REMOVAL OF SO₂ GAS

[75] Inventors: Kazumasa Tezuka; Seiichi Hisano; Hyoichi Sasaki; Ikuo Watanabe, all of Okayama, Japan

[73] Assignees: Dowa Mining Co. Ltd., Tokyo; Dowa Engineering Co. Ltd., Okayama, both of Japan

[21] Appl. No.: 27,891

[22] Filed: Apr. 6, 1979

Related U.S. Application Data

[63] Continuation-in-part of Ser. No. 831,124, Sep. 7, 1977, abandoned.

[30] Foreign Application Priority Data

Sep. 11, 1976 [JP]  Japan .................................. 51-108990

[51] Int. Cl.³ .................... C01B 17/00; G01N 25/48
[52] U.S. Cl. ................... 423/242; 23/230 R; 23/230 A
[58] Field of Search ............... 23/230 R, 230 A; 423/242 A, 166, 555, 556, 242 R

[56] References Cited

U.S. PATENT DOCUMENTS

| | | | |
|---|---|---|---|
| 1,663,435 | 3/1928 | Bradner | 423/556 X |
| 3,138,436 | 6/1964 | Harmon | 23/230 R X |
| 3,716,333 | 2/1973 | Peushel et al. | 23/230 R |
| 3,768,973 | 10/1973 | Wasilewski | 23/230 R |
| 3,888,726 | 6/1975 | Hultman | 23/230 R X |
| 3,943,230 | 3/1976 | Yamamichi et al. | 423/242 A |
| 4,162,299 | 7/1979 | Takeyama et al. | 423/242 R |

*Primary Examiner*—Arnold Turk
*Attorney, Agent, or Firm*—Toren, McGeady and Stanger

[57] ABSTRACT

Reaction heat values of basic aluminum sulfate solution with acid such as sulfuric acid are correlative with an amount of base contained in said solution. The difference of temperatures of said solution before and after its reaction with said acid is utilized as an indication for the calibration of the basic amount in the solution. This calibration is effectively utilized for the control of the basic amount of said solution which is employed in the removal of SO₂ gas from a waste gas.

5 Claims, 8 Drawing Figures

METHOD FOR MEASURING THE BASIC AMOUNT IN BASIC ALUMINUM SULFATE SOLUTION FOR REMOVAL OF SO₂ GAS

This is a continuation-in-part of U.S. patent application Ser. No. 831,124, filed Sept. 7, 1977, now abandoned, the contents of which are incorporated herein by reference.

BACKGROUND OF THE INVENTION

1. Field of the Invention

This invention relates to a method of measuring the basic amount contained in a basic aluminum sulfate solution which is employed in the removal of SO₂ gas.

2. Description of the Prior Art

A solution of basic aluminum sulfate is produced when an aluminium sulfate solution is neutralized with a neutralizing agent, such as, calcium carbonate. Basic aluminum sulfate may be represented by the following chemical formula (1).

$$Al_2(SO_4)_3 \cdot nAl_2O_3 \tag{1}$$

The amount of aluminum expressed as $Al_2O_3$ in the above formula is termed the "basic amount," and is generally expressed in g/l. It is also widely known that the ratio of the basic amount with respect to the total amount of aluminum in a solution of basic aluminum sulfate is termed the "basicity." This basicity is calculated by the following expression (2).

$$\text{Basicity} = \frac{\text{basic amount}}{\text{total amount of aluminum in solution}} \times 100(\%) \tag{2}$$

In order to calculate the basic amount in a solution of basic aluminum sulfate, pH measurements, electrical conductivity, and the like have been utilized. In this instance, there is a ternary relation between the calculated amount, the aluminum concentration, and the basic amount. Therefore, with these conventional methods, it is essential to thoroughly understand the ternary relationships in the solution. In addition, since the conventional methods are greatly influenced by impurities in the solution, accurate measurement of basic amount of a solution and its consequent basicity cannot easily be made.

Figure 2:
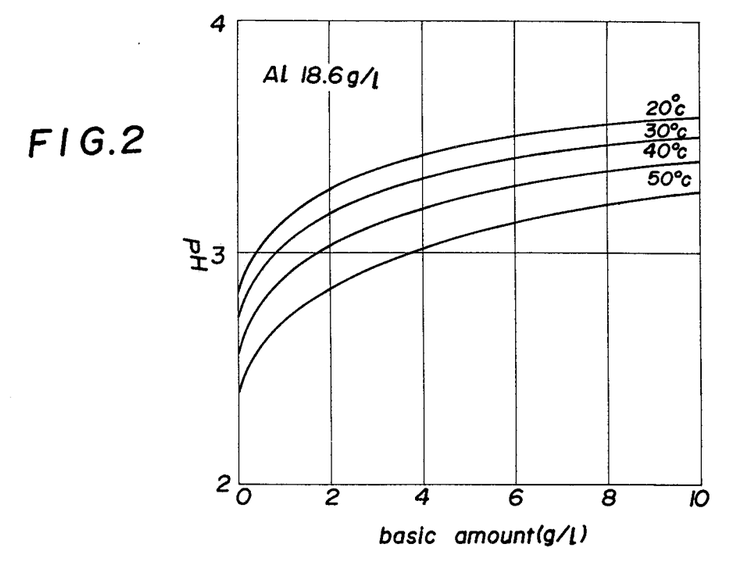
FIG. 2 is a diagram similar to FIG. 1 showing the relationship of the pH measurement to the basic amount.
Figure 3:
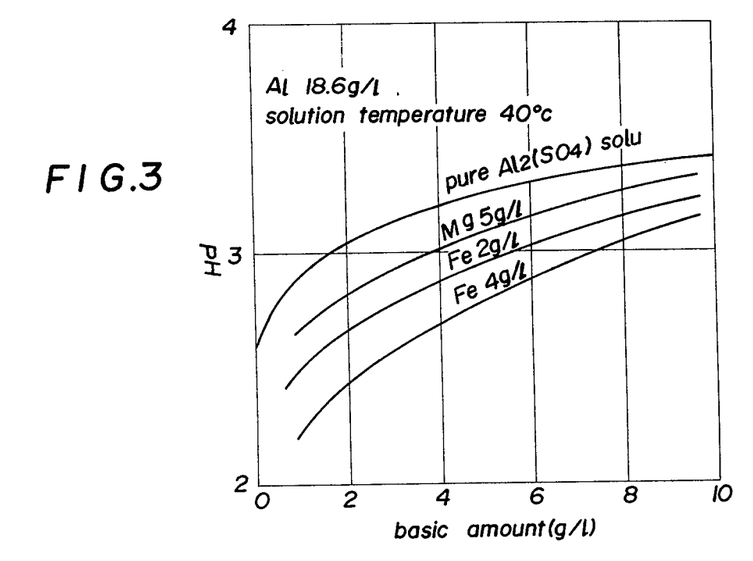
FIG. 3 is a diagram similar to FIG. 2, wherein the solution contains impurities.
Figure 4:
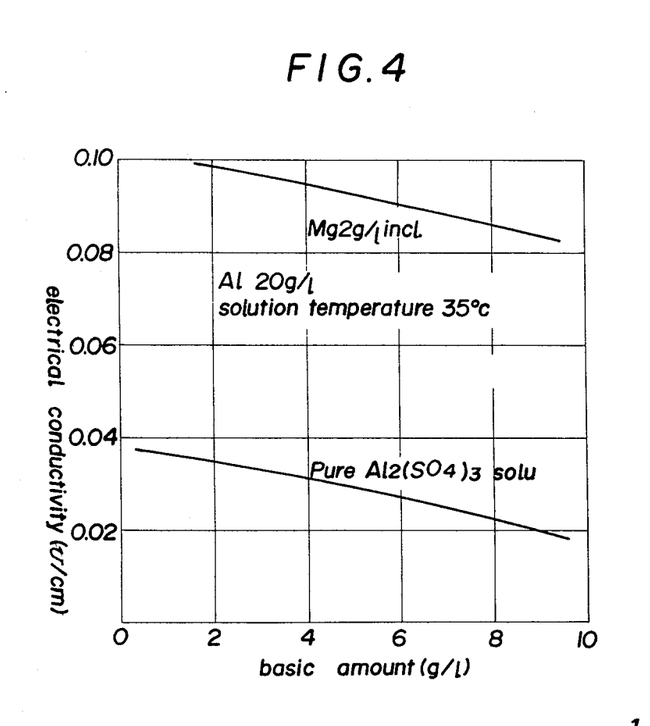
FIG. 4 is a diagram showing the relation between the basic amounts of solutions and the electric conductivities thereof.

The drawbacks of the above-mentioned conventional methods are visibly explained in FIGS. 2 to 4. FIG. 2 in which the relation between pH measurements and basic amounts is diagrammatically illustrated, shows that in comparison to comparatively large differences of the basic amounts of solutions, the difference in the pH values thereof is extremely small, viz, the difference of 2 g/l of basic amount is represented by a difference of only 0.2 to 0.3 corresponding pH values, said latter difference being too small for accurate measurement. FIG. 3 shows that the calibration of the basic amount contained in basic aluminum sulfate solutions by means of pH measurements is adversely affected by impurities contained in the solution, and one has to compensate for such impurities. In FIG. 4, which diagrammatically shows the relations between the basic amounts and the electrical conductivities of a pure solution in the range of ±2 g/l of basic amount. At about 4 g/l, the difference in conductivity is only ±13%, and said difference is as small as ±4.3% in case of a solution containing 2 g/l of Mg. This means that a calibration method by means of the measurement of electrical conductivity of a solution is not reliable.

The ability to easily and precisely to control basicity is particularly important when considering continuous processes. Thus, not every method allows for the continual measurement of the basicity without resulting in disruptions in the process, decreases in the efficiency and/or excessive variation in the process conditions and, in turn, the products or results produced.

Of special importance, in this respect, in the process wherein SO₂ is removed from waste gases by absorption in a solution of basic aluminum sulfate. Such a process is carried out continuously and unless the basicity of the solutions generated and used during the process can be precisely controlled within specified limits, the process cannot be successfully carried out efficiently.

SUMMARY OF THE INVENTION

The present inventors have found that the heat produced when sulfuric acid is added to and reacted with a solution of basic aluminum sulfate has a specific relationship to the basic amount of said solution. Thus, in the present invention, the basic amount of a solution is directly obtained by the calibration of the temperature difference of the solution before and after its reaction with sulfuric acid.

Particularly, in the present invention, a calibration curve is predetermined for a series of solutions having differing known basic amounts. Thus, the solutions are prepared and the temperature measured. At least stoichiometric amount of sulfuric acid is then added to react with the basic amount (this reaction takes place essentially immediately) and the temperature is measured again. The difference in temperature ΔT is calculated. A graph can then be prepared of the relationship of ΔT to the basic amounts.

Thereafter, the same procedure can be carried out on the actual solution to be analyzed and from the ΔT thus obtained, the actual basic amount can be obtained from the predetermined calibration curve.

More specifically, a solution of basic aluminum sulfate reacts with sulfuric acid in the manner expressed in reaction sequence (3) and produces reaction heat Q.

$$Al_2(SO_4)_3 \cdot nAl_2O_3 + 3nH_2SO_4 \rightarrow (1+n)Al_2(SO_4)_3 + 3nH_2O + Q \tag{3}$$

This reaction heat Q causes the temperature difference of the solution before and after the carrying out of chemical reaction. Said temperature difference ΔT can be expressed in the following equation (4), wherein a heat capacity of the reaction system is made as C.

$$\Delta T(°C.) = \frac{Q\ (cal)}{C\ (cal/°C.)} \tag{4}$$

This difference is utilized in the present invention for the measurement of the basic amount of the solution.

We have particularly discovered that the method of the present invention is extremely successful in processes for the removal of SO₂ from waste gases wherein the waste gas is contacted with a solution of basic aluminum sulfate to absorb the SO₂, this solution is then subjected to oxidation conditions to convert any sulfite to sulfate, a major portion of this first solution thus treated is returned to the absorption step and the remainder is treated with CaCO₃ or Ca(OH)₂ to precipitate gypsum which is separated and this second solution is returned to the absorption step. The basicity of the first and second solutions may be easily and precisely determined and monitored in a continuous manner and the process can thus be carried out in an extremely efficient manner.

DESCRIPTION OF THE PREFERRED EMBODIMENTS

Figure 1:
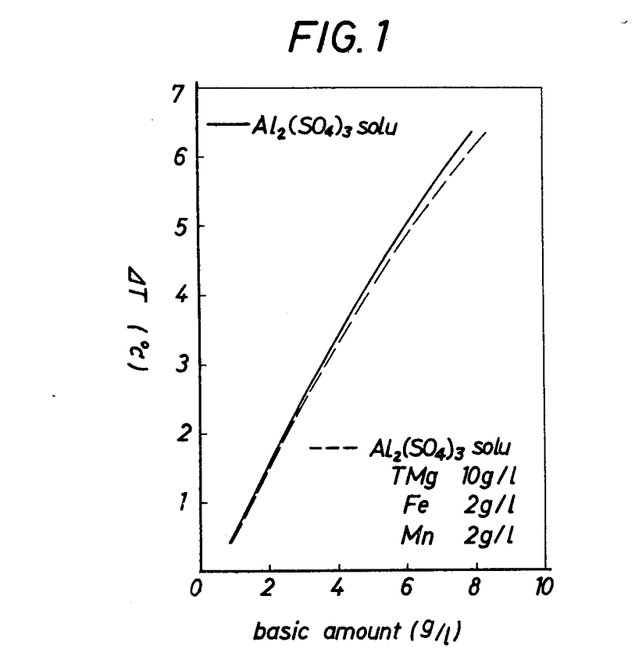
FIG. 1 is a diagram showing the relationship between $\Delta T$ and the corresponding basic amount of solutions in accordance with this invention.

Firstly, it shall be noted from FIG. 1 for example that the relation between the basic amount and the difference of temperatures of a solution changes lineally, and that the total concentration of aluminum in the solution does not correlate to this relationship.

The aforementioned linear correlationship between the basic amount and the difference of temperature of a solution has been confirmed by the present inventors through a number of experiments including those for FIG. 1, which were conducted by employing solutions containing total amounts of aluminum in concentration varying from 5–50 g/l, basic amounts of 0–25 g/l, and temperatures before the reaction from 20° C. to 60° C., and by utilizing acids such as, sulfuric acid at concentrations of 0.01–36 N at ratios to the solution between 1:1 to 10:1.

The diagram of FIG. 1 is based on an experiment, in which a series of sample solutions containing basic amounts of 1–8 g/l were used and in which the concentration of sulfuric acid was 6 N and the ratio of the amount of solution to be measured to the amount of acid was 6:1, since this amount of acid is sufficient on a stoichiometric basis to the basic amount of 9 g/l. In other words, if the basic amount is expected to be more than 9 g/l in a solution, said amount of acid is insufficient for carrying out this invention. It is also noted from FIG. 1 that the relationship is almost the same between the pure solution of basic aluminum sulfate (a solid line) and the impure solution (dotted line). This means that the accuracy of the present invention method is not affected by the impurity of the solution.

The volume ratio of sulfuric acid to be added to a solution can easily be determined in view of a possible maximum basic amount which is expected in the solution. Though the physical or mechanical control for maintaining said ratio seems rather important because supplying sulfuric acid in an amount in excess of the ratio would inevitably cause variation in the heating value per heat capacity of the solution, the aforementioned series of experiments show that such variation is negligible so long as the supply of sulfuric acid is controlled with ±5% of the predetermined volume ratio of acid to the solution. In other words, a difference of supply volume of sulfuric acid to the solution of ±5% of a predetermined volume gives a deviation of only ±0.5% from the actual basic amount in the solution. Hence, the accuracy of the volumetry of a basic amount by the present invention method is not largely influenced by a deviation of the volume ratio between the sulfuric acid and the solution to be analyzed. This method can thus be safely used in a continuous flow calibration or a Batch type volumetry.

It was also determined whether or not a difference of concentration of sulfuric acid from a predetermined concentration adversely affects the calibration of the basic amount of a given solution. It is noticed that even when a concentration of the acid differs by ±10% from a predetermined concentration, the deviation of the measurement of basic amounts is only ±0.05 g/l. In other words, such difference is negligible in this invention. It was found that while highly concentrated sulfuric acid would bring about a temperature rise of a solution because of the heat of dilution, such temperature rise is negligible when the concentration of sulfuric acid is lower than 20 N. It shall be noted also that when extremely low concentrations of sulfuric acid are utilized on the other hand, accurate calibration in accordance with the invention can hardly be made, because such low concentrations of sulfuric acid require a considerably large volume of solution to constitute a stoichiometric amount to an expected basic amount. This results in an increase in the total amount of solution after reaction and consequent increase in the heat capacity of the solution and a decrease in $\Delta T$. The aforementioned experiments show that in practice, the minimum concentration of sulfuric acid is 0.05 N to obtain a sufficient $\Delta T$ to be obtained for the purposes of this invention.

For example, in a process for removing sulfur oxide from waste gas by using a solution of basic aluminum sulfate, such as, described in U.S. Pat. No. 3,943,230, sulfuric acid of 3–8 N, preferably 4–5 N is utilized for determining the basic amounts of each stage in accordance with this invention.

Figure 5:
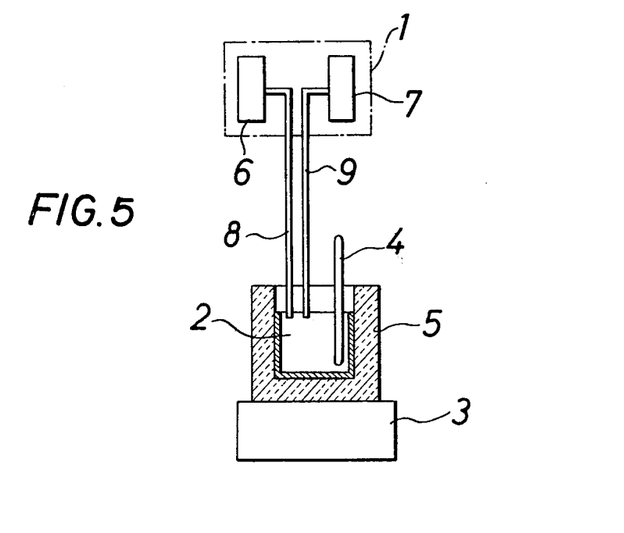
FIG. 5 is a schematic view of a Batch type apparatus for use in carrying out the inventive method.

A Batch type volumetric method in accordance with the present invention method is explained hereinunder with reference to FIG. 5. An apparatus as illustrated in FIG. 5 consists of a constant temperature bath 1, reaction vessel 2, oscillating platform 3, thermometer 4, insulator 5, vessel for storing a solution to be measured at a predetermined volume 6, vessel for storing sulfuric acid at a predetermined volume 7, pipe for the solution 8, and a pipe for sulfuric acid supply 9. Under such constructions, a specific amount of the solution contained in the vessel 6 is supplied to the reaction vessel via the pipe 8, whereby the temperature of the solution is measured by the thermometer 4. Subsequently, sulfuric acid contained in the vessel 7 is supplied at a specific amount to the reaction vessel 2 through the pipe 9, whereby it reacts with the solution. This provides the difference in temperatures of the solution for obtaining the basic amount of the solution.

Apparatus for the continuous volumetry in accordance with the present invention is explained with reference to FIG. 6. In this figure, numeral 10 indicates a supply pipe of the solution, 11 a supply pipe of sulfuric acid, 12 and 13, respectively, helical portions of the pipes 10 and 11, 14 a constant temperature bath housing said helical pipe portions 12 and 13, 15 a vessel for measuring the temperature of solution, and 16 a reaction vessel. Vessels 15 and 16 are provided with thermometers 17 and 18. The outlet end of the pipe 10 is connected to the vessel 15, while the vessels 15 and 16 are connected to each other by a pipe 19.

The solution is continuously supplied to pipe 10 at a constant volume, kept at a constant temperature within the bath 14, and then its temperature is measured at the vessel 15. The solution then enters into the reaction vessel 16 wherein it is mixed with sulfuric acid. The temperature of reacted solution is measured at vessel 18, and exhausted outside of pipe 10. The difference of temperatures measured by thermometers 17, 18 is an indication of the basic amount of the solution. Such temperature differences can be indicated electrically, for example, by means of meters, and can be utilized for the control of a neutralizing process for producing a desired basic aluminium sulfate solution.

If the total aluminum concentration of the solution is known, the basic amount obtained in accordance with this invention can readily be utilized for obtaining the basicity of the solution by means of the aforementioned expression (2).

EXAMPLE 1

Batch type apparatus as illustrated in FIG. 5 is employed. 100 ml of basic aluminum sulfate solution, temperature of which is kept at 40° C. by the constant temperature bath 1 of 40° C.±0.1° C., is supplied to reaction vessel 2, whereby it is reacted with 17 ml of sulfuric acid (6 N) of 40° C. The difference of temperatures of the solution before and after said reaction is measured by means of a Beckmann thermometer. The basic amounts of four different sample solutions are obtained based on the difference of temperatures. To wit, the difference of temperatures of each sample solution thus obtained were compared with the diagram of FIG. 1. Their results are enumerated in Table 1. These basic amounts are compared with the chemically analyzed values of the basic amounts of the same solutions. These values are the average of five analyses for each solution.

TABLE 1

| Solution | | Present method | Chemical analysis |
|---|---|---|---|
| Basic | 1 | 2.1 | 2.2 |
| amount | 2 | 5.0 | 5.1 |
| (g/l) | 3 | 6.9 | 7.1 |
| | 4 | 8.4 | 8.7 |

It is noted that the basic amounts measured by this invention method are very close with those obtained by chemical analysis. The values in accordance with this invention are slightly less than the chemical analytical values, because of errors introduced by the thermal capacities of the reacting vessels, thermometers and equipment used.

EXAMPLE 2

Figure 6:
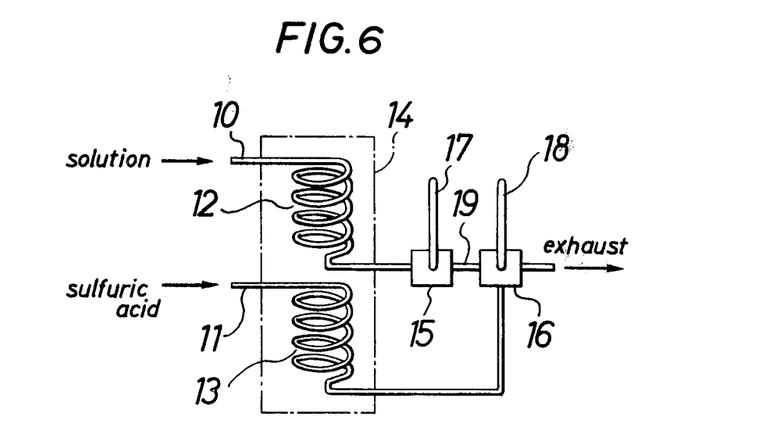
FIG. 6 is a view similar to FIG. 5, in which the basic amount of a solution is continuously measured.

Apparatus such as illustrated in FIG. 6 was employed in this example, in which the helical pipe portions 12, 13 are teflon tubes of 5 m of length and 2 mm of inner diameter, respectively. They are housed in the constant temperature bath which is kept at 40° C. by warm water. The vessel 15 is a glass vessel having the volume of 5 ml, and the reaction vessel has a volume of 30 ml. The solution and sulfuric acid are supplied by a pump at rates of 30 ml/min. and 5 ml/min., respectively. The total aluminum concentration of the solution is 10-20 g/l, and the concentration of the employed sulfuric acid is 6 N. The vessels 15 and 16 are thermally insulated by means of suitable insulating materials. Thermistors contained in glass tubes are employed as the thermometers 17, 18, which constitute a bridge circuit. The difference of temperature is obtained directly from the output of the bridge circuit.

As in Example 1, several experiments are made. Table 2 shows the results. The results are those obtained by comparison of the difference of temperatures to the diagram of FIG. 1.

TABLE 2

| Solution | | Present method | Chemical analysis |
|---|---|---|---|
| Basic | 1 | 2.3 | 2.3 |
| amount | 2 | 5.0 | 5.1 |
| (g/l) | 3 | 7.2 | 7.1 |
| | 4 | 8.5 | 8.7 |

EXAMPLE 3

In order to affirm the superiority of this invention method to conventional methods, basic amounts of different solutions are measured by this and the conventional methods. Their results are enumerated in Table 3.

TABLE 3

| | Solution No. | (Values in g/l) 1 | 2 | 3 |
|---|---|---|---|---|
| | 1st | 1.25 | 4.82 | 8.66 |
| | 2nd | 1.24 | 4.83 | 8.65 |
| Method 1 | 3rd | 1.23 | 4.82 | 8.67 |
| | deviation | 0.5% | 0.1% | 0.1% |
| | average | 1.24 | 4.82 | 8.66 |
| | 1st. | −3.4 | 7.6 | 5.2 |
| | 2nd | 3.2 | 2.3 | 11.1 |
| Method 2 | 3rd | 2.5 | 3.5 | 6.3 |
| | deviation | — | 47% | 32% |
| | average | 0.77 | 4.47 | 7.53 |
| | 1st | 7.6 | 6.3 | 8.5 |
| | 2nd | −8.3 | 10.5 | 4.2 |
| Method 3 | 3rd | 5.2 | −3.0 | 12.3 |
| | deviation | — | 110% | 33% |
| | average | 1.50 | 4.60 | 8.33 |

Solutions 1, 2, 3 are subjected to three different methods, three times each. Method 1 is the one conducted in accordance with the present invention. Method 2 is one of the typical conventional methods, in which the total aluminum amounts of basic aluminum sulfate solutions are obtained by chelatometry using EDTA, and sulfuric acid radicals are measured by gravity titration with barium sulfate, whereby the corresponding basic amounts are calculated. Another conventional method 3 is similar to the method 2, except that acid-base titration with caustic soda solution is utilized for measuring acid radicals.

It shall be noted from the above Table 3 that calibration errors are extremely small in this invention method, compared to other methods. The other methods, especially the method 2 has such additional drawbacks that when the solution contains impurities, such as, Na, Mg and others, the amount of sulfuric acid radicals which have been measured has to be compensated in view of those radicals which are to be combined with ions of the impurities. This step makes this conventional method more hazardous.

EXAMPLE 4

The present invention method was employed in connection with the control of a basicity of a continuously circulating flow of a basic aluminum sulfate solution which was used in a process for removing sulfur dioxide gas contained in a waste gas. Such a process is described in U.S. Pat. No. 3,943,230 of the present applicant.

A process of this kind comprises the steps of:

(1) absorbing $SO_2$ gas contained in a waste gas in a basic aluminum sulfate solution in an absorbing tower:

(2) oxidizing the solution to convert sulfite ions in the solution to sulfate ions, a major portion of the solution thus oxidized is returned to the absorbing tower of step (1);

(3) a part of the oxidized solution is sent to a neutralizing bath wherein the solution is neutralized by the addition of calcium carbonate or calcium hydroxide to precipitate gypsum; and (4) separating the gypsum and returning the solution as the absorbent solution to the absorbing tower of the step (1).

The efficiency of this process largely depends upon the basicity of the solution which is circulated in steps 2 and 4. To wit, when the basicity of the solution which is returned from step (2) to step (1) becomes less than 5%, the absorbtion of $SO_2$ gas by the solution in step (1) is minimal and efficiency is decreased; and when the basicity of the solution in step (4) becomes more than 40%, the amount of aluminum which adheres to the gypsum increases, resulting in larger loss of aluminum.

Hence, the basicity of the aforementioned major part of the solution oxidized in step (2) and returned to the absorbing tower of the step (1) is kept so as to be no lower than and preferably at about 5% by calibrating the basic amount of said solution by the present method and calculating the basicity with reference to the thus obtained basic amount and the aforementioned expression (2). In the same manner, the basicity of the solution from the step (3) to the step (4) is kept so as to be lower than 40% and preferably, about 30%.

As a specific example, waste gas containing 1,000 ppm of $SO_2$ was passed through an absorbing tower 0.6 m in diameter and 4 m in height at a rate of 1,000 m$^3$/hr. The basicity of the solution being returned from step (2) to step (1) is measured in accordance with this invention and kept so as to be 5% by controlling the amount of flow of the solution from step (2) to step (3).

The basicity of the solution from step (3) to step (4) is also calibrated in accordance with this invention and kept so as to be 30% by controlling the amount of neutralizing agent used in step (3). The operating conditions of the apparatus as illustrated in FIG. 6 are as follows.

Figure 7:
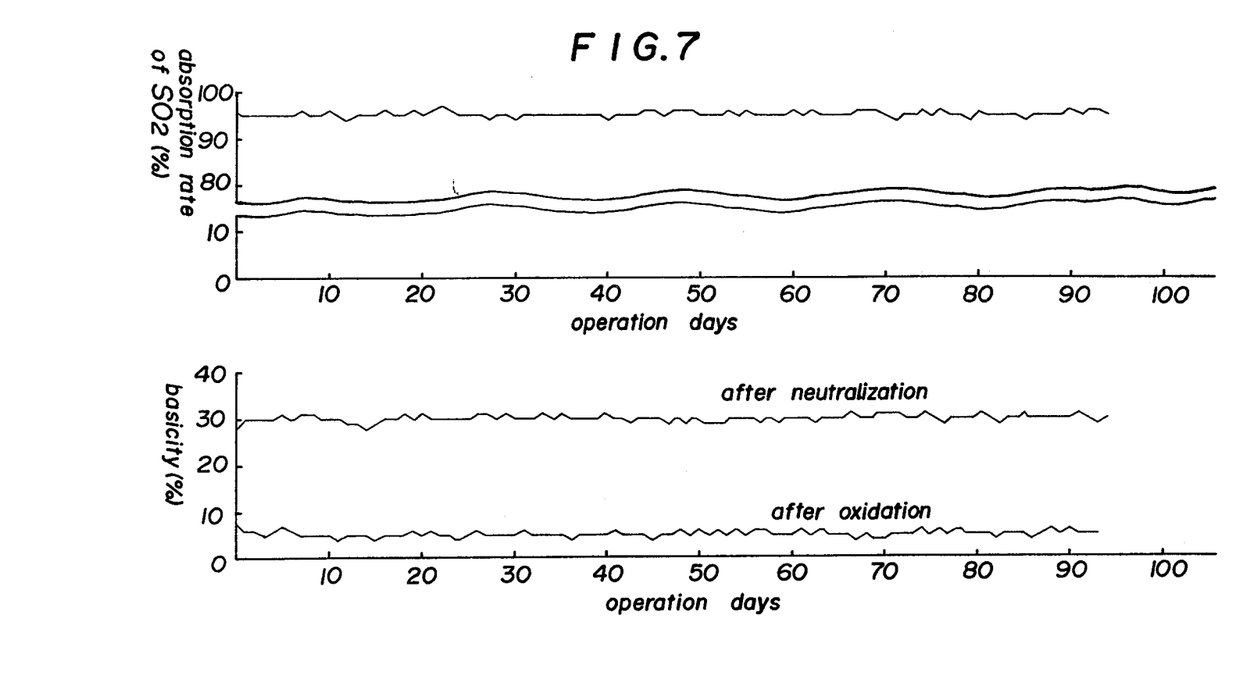
FIG. 7 is a graph showing the efficiencies of a solution for absorbing $SO_2$, when the basicity of the solution is controlled in accordance with this invention.
Figure 8:
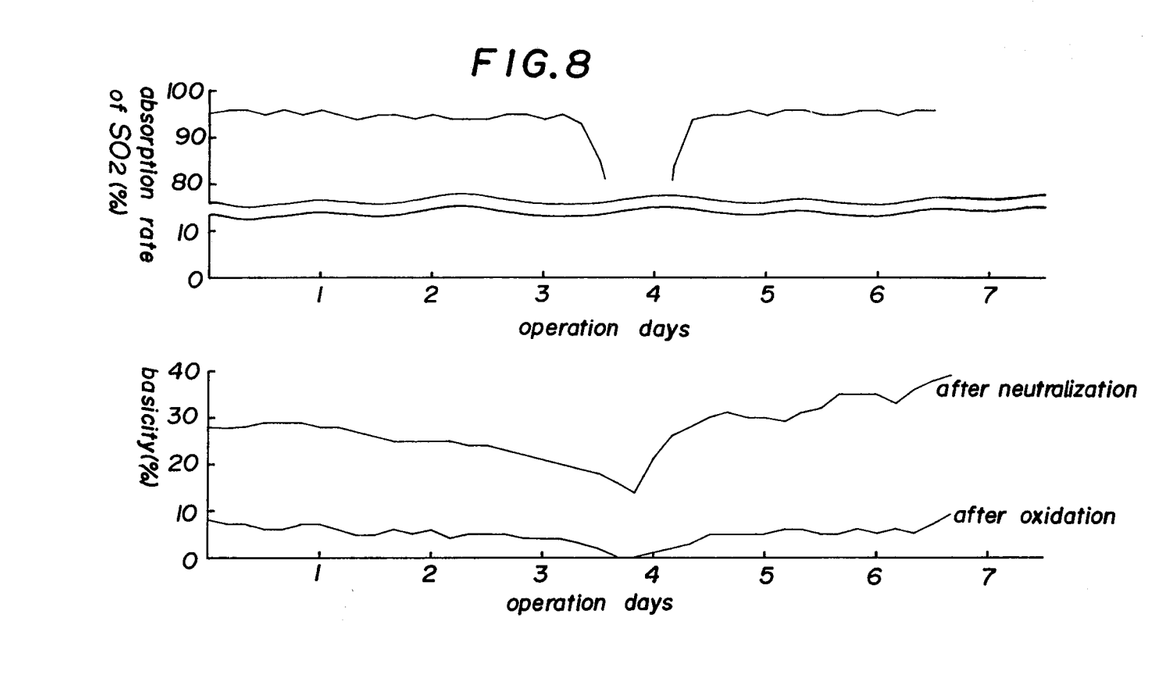
FIG. 8 is a graph similar to FIG. 7, wherein the control of the basicity of the solution is made by pH-measurement of the solution.

Amount of sampling solution: 20 ml/min.
Sulfuric acid (5 N): 3.2 ml/min.
Temperature of constant temperature bath: 40° C.
Aluminum amount or concentration in the solution: 10 g/l The operational efficiencies of the removal of $SO_2$ gas from waste gas by means of the basic aluminum solution were kept high and constant when the basicity of the solution was measured continuously in accordance with this invention (FIG. 7). In contrast, FIG. 8 shows the insufficient and irregular absorption of $SO_2$ by the solution obtained when the basicity was controlled by the pH measurement and which resulted in the stoppage of operation in 7 days.

It shall be noted from the above that calibration errors are extremely small in this invention method, compared to other methods. The other methods have such additional drawbacks that when the solution contains impurities, such as, Na, Mg and impurities, the amount of sulfuric acid radicals which have been measured must be compensated for in view of those radicals which are to be combined with ions of the impurities. This step makes this conventional method more hazardous.

What is claimed is:

1. A method for removing $SO_2$ from a waste gas comprising:
   (1) contacting the waste gas with a basic aluminum sulfate solution which absorbs the $SO_2$ from the gas;
   (2) subjecting the solution with the absorbed $SO_2$ gas therein to oxidation to convert any sulfite ion to sulfate;
   (3) returning a major portion ($P_1$) of the oxidized solution to the absorbing step;
   (4) neutralizing the remainder of the oxidized solution with calcium carbonate or calcium hydroxide to precipitate gypsum which is separated to produce solution ($P_2$);
   (5) returning solution ($P_2$) to the absorbing step; and controlling the amounts of basic aluminum sulfate at desired levels in solutions $P_1$ and $P_2$ by
      (a) obtaining samples of solutions $P_1$ and $P_2$
      (b) measuring the temperatures $T_1$ and $T_{1'}$ of the sample solutions $P_1$ and $P_2$, respectively;
      (c) adding sulfuric acid to each of sample solutions $P_1$ and $P_2$ in amounts at least equivalent, on a stoichiometric basis to the estimated basic amount in each solution and immediately measuring the respective temperatures $T_2$ and $T_{2'}$ of the mixtures;
      (d) determining the basic amount for each respective solution from the temperature differences $T_1$ and $T_2$, and $T_{1'}$ and $T_{2'}$ from a predetermined calibration curve of the linear relationship of temperature difference and basic amount; and
      (e) adjusting the basic amounts in solutions $P_1$ and $P_2$ to the desired levels based on said determination.

2. The method of claim 1 in which the basic amount thus determined is related to basicity of solutions $P_1$ and $P_2$ by the expression $$\text{Basicity} = \frac{\text{basic amount}}{\text{total amount of aluminum in solution}} \times 100(\%)$$

and the basicity of solution $P_1$ is kept at not less than about 5% and the basicity of solution $P_2$ is kept at not more than about 40%.

3. The method of claim 1 or 2 wherein an electric current is generated in dependence on the respective temperature differences, the electric current being related to a predetermined calibration and determining said basic amount therefrom.

4. The method of claim 1 or 2 wherein the sulfuric acid concentration is between about 3 to 8 N.

5. The method of claim 1 or 2 wherein the sulfuric acid concentration is between about 4 to 5 N.

* * * * *